United States Patent
Monahan et al.

(10) Patent No.: US 7,201,898 B2
(45) Date of Patent: Apr. 10, 2007

(54) METHODS AND COMPOUNDS FOR CONTROLLED RELEASE OF RECOMBINANT PARVOVIRUS VECTORS

(75) Inventors: Paul E. Monahan, Chapel Hill, NC (US); Richard Jude Samulski, Chapel Hill, NC (US); Joseph E. Rabinowitz, Carrboro, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 14 days.

(21) Appl. No.: 10/276,501

(22) PCT Filed: Jun. 1, 2001

(86) PCT No.: PCT/US01/17898

§ 371 (c)(1),
(2), (4) Date: Dec. 19, 2002

(87) PCT Pub. No.: WO01/91803

PCT Pub. Date: Dec. 6, 2001

(65) Prior Publication Data

US 2004/0013645 A1   Jan. 22, 2004

Related U.S. Application Data

(60) Provisional application No. 60/208,702, filed on Jun. 1, 2000.

(51) Int. Cl.
*A61K 48/00* (2006.01)
*A61F 2/00* (2006.01)

(52) U.S. Cl. ...................... 424/93.2; 424/423
(58) Field of Classification Search .............. 435/320.1
See application file for complete search history.

(56) References Cited

U.S. PATENT DOCUMENTS 5,658,785 A   8/1997   Johnson
5,869,306 A   2/1999   Kuma et al.
6,333,194 B1 * 12/2001 Levy et al. ................ 435/450

2003/0053990 A1 *  3/2003 Rabinowitz et al. ....... 424/93.2
2003/0108525 A1 *  6/2003 Sista et al. ................. 424/93.2

FOREIGN PATENT DOCUMENTS

| WO | WO 94/29471 |   | 12/1994 |
| WO | WO 98/41240 | * |  9/1998 |
| WO | WO 00/41731 |   |  7/2000 |
| WO | WO 00/43044 |   |  7/2000 |
| WO | WO 01/09360 |   |  2/2001 |

OTHER PUBLICATIONS

Siemens et al., J. Natl. Cancer Inst. vol. 92 No. 5, pp. 403-412 (2000).*
Croyle et al. Pharmaceutical Development and Technology 3/3: 373-383 (1998).*
Verma et al. Nature 389:239-242 (1997).*
Palu et al. J. Biotechnol. 68:1-13 (1999).*
Fox, ASM News , Feb. 2000, 66 (2): 1-3.*
Monahan, et al., abstract, "Stability of recombinant adeno-associated virus vectors permits delivery on implantable matrices," *Blood*, 96(11 Part I): 525a (2000).
Nybert-Hofman et al., "Instability of adenoviral vectors during transport and it's implication for clinical studies," *Nature Medicine* 3(4): 955957 (1999).
Siemens, et al.; "Viral Vector Delivery in Solid-State Vehicles: Gene Expression in a Murine Prostate Cancer Model," *Journal of National Cancer Institute*, 92(5): 403-412 (2000).
Airu et al., "Molecular bypass, the application of VEGF to gene therapy of limb ischemia;" *Natl Med J China*; 76: 9; 662-665 (1996). (Abstract in English only; Chinese language document.).
Qin et al., "Gene suture—a novel method for intramuscular gene transfer and its application in hypertension therapy," *Life Sciences*; 65: 21; 2193-2203 (1999).

* cited by examiner

*Primary Examiner*—Nancy Vogel
(74) *Attorney, Agent, or Firm*—Myers Bigel Sibley and Sajovec, PA

(57) ABSTRACT

The invention uses recombinant parvoviruses, and particularly recombinant adeno-associated virus (rAAV) to deliver genes and DNA sequences for gene therapy following manipulation of the therapeutic virus for packaging and transport. The invention delivers therapeutic viral vectors via rAAV affixed to support matrixes (i.e., sutures, surgically implantable materials, grafts, and the like).

47 Claims, 6 Drawing Sheets

METHODS AND COMPOUNDS FOR CONTROLLED RELEASE OF RECOMBINANT PARVOVIRUS VECTORS

RELATED APPLICATIONS

This application claims priority under 35 U.S.C. §371 from PCT Application No. PCT/US01/17898 (published under PCT Article 21(2) in English), filed on Jun. 1, 2001, which claims the benefit of U.S. Provisional Application No. 60/208,702, filed on Jun. 1, 2000; the disclosures of which are incorporated by reference herein in their entireties.

FEDERAL SUPPORT OF THE INVENTION

This invention was made with government support under grant number DK54419 from the National Institutes of Health. The United States government has certain rights to this invention.

FIELD OF THE INVENTION

This invention relates to the controlled release of parvovirus vectors, and particularly the controlled in vivo release of recombinant adeno-associated (rAAV) viral vectors.

BACKGROUND OF THE INVENTION

The preparation and administration of many drugs and therapeutic proteins following freeze-drying (lyophilization) is known. Advances in polymer chemistry and biomaterials have achieved the delivery of drugs via attachment to graft materials. For example, heparin and urokinase bonding to vascular graft materials has been used in an attempt to improve long-term patency of vascular grafts. Chemotherapy drugs have been impregnated into wafers for time-release delivery. None of these systems, however, deliver DNA with the goal of persistent therapeutic protein expression in the host cells.

Known viral and non-viral (e.g. lipid-mediated, electroporation-enhanced) gene therapy delivery systems rely on the delivery of gene vectors in solutions. The solutions may be injected intravenously, intramuscularly, subcutaneously, or may even be administered orally. These approaches are hampered by the fact that many gene therapy vectors or formulations are not stable (i.e., they lose the ability to infect cells and deliver DNA) when the vector is exposed to alterations in conditions like temperature, hydration, or pH. In addition, these routes may lead to undesirably rapid biodistribution of the delivered virus to organs distant from the tissue of delivery (e.g., within seconds after intravenous delivery, or within minutes to hours after intramuscular delivery). Accordingly, a need exists for methods in which gene delivery may be accomplished in a time-controlled or delayed manner, and potentially with delayed biodistribution of virus distant from the target tissue.

Adeno-associated virus (AAV) is a nonpathogenic, helper-dependent member of the parvovirus family. One of the identifying characteristics of this group is the encapsidation of a single-stranded DNA (ssDNA) genome. The separate plus or minus polarity strands are packaged with equal frequency, and either is infectious. At each end of the ssDNA genome, a palindromic terminal repeat (TR) structure base-pairs upon itself into a hairpin configuration. This serves as a primer for cellular DNA polymerase to synthesize the complementary strand after uncoating in the host cell. Adeno-associated virus generally requires a helper virus for a productive infection. Although adenovirus (Ad) usually serves this purpose, treatment of AAV infected cells with UV irradiation or hydroxyurea (HU) will also allow limited replication.

Recombinant AAV (rAAV) gene delivery vectors also package ssDNA of plus or minus polarity, and must rely on cellular replication factors for synthesis of the complementary strand. While it was initially expected that this step would be carried out spontaneously, by cellular DNA replication or repair pathways, this does not appear to be the case. Early work with rAAV vectors revealed that the ability to score marker gene expression was dramatically enhanced when cells were co-infected with adenovirus, or transiently pretreated with genotoxic agents. Similar induction of rAAV vectors has been observed in vivo following treatment with Ad, ionizing radiation, or topoisomerase inhibitors. However, the effect was highly variable between different tissues and cell types.

The effort to establish the efficiency of AAV-mediated gene delivery following complete desiccation was described by Rabinowitz et al. in May, 1998 at the Third International Cancer Gene Therapy Meeting. At that time, it was shown that recombinant AAV remains infectious and competent for transduction (gene delivery leading to expression of the transgenic protein) in a broad range of temperatures, pH, and hydration states. Since that time, the present inventors have performed additional studies of AAV-mediated gene delivery following desiccation of the virus, based upon the reasoning that one limitation of gene therapy with viral vectors delivered to the bloodstream, or even delivered locally to tissues like the lung or muscle in large doses, is virus scatter to many sites beyond the intended site of action.

One disadvantage of virus scatter is that generally, too little of the therapeutic gene is present or delivered to the site where it is intended. For example, a CFTR gene intended to be delivered to the lung as a treatment for cystic fibrosis will have decreased utility if most of the virus goes to the liver and spleen. Another problem with known gene delivery systems is that it is difficult to judge an accurate dosage of the gene vector required to achieve the desired therapeutic effect. Finally, if the viral vector has potentially toxic effects upon exposure to organs outside of the target, it is desirable to localize the therapeutic treatment to the target only and decrease viral scatter. A persistent concern with gene therapy is the theoretical possibility of unwanted gene delivery vector spreading to subjects' gonads, thus perhaps leading to insertional mutagenesis to germline cells. Accordingly, precise direction and amount of delivery of gene therapy vectors continues to be a priority in the development of safe and reliable gene delivery systems.

SUMMARY OF THE INVENTION

The invention uses recombinant parvoviruses, and in particular, recombinant adeno-associated virus (rAAV) to deliver nucleic acid sequences (i.e., genes and DNA sequences) for gene therapy following a dehydration or drying step (i.e., partial or complete desiccation, lyophilization) in which the therapeutic virus vector is dried onto (i.e., affixed to) a support matrix. Useful support matrices include surgically implantable materials (i.e., sutures, surgical graft material, implantable devices and the like) for packaging and transport to a subject, thus allowing delivery of gene therapy via the rAAV affixed to the support matrixes.

The present inventors have extensively characterized the use of the adeno-associated virus in solution as a gene transfer vector. The present investigations characterizing the extraordinary stability of rAAV as compared to other gene transfer viruses have led to the development of strategies to dehydrate the virus for purposes of achieving stable transport of the virus, and drying rAAV onto implantable materials (e.g., sutures, graft materials and other surgically implantable materials), in order to directly apply the virus to specific and local tissue sites for gene therapy.

The stability of rAAV over a range of conditions of hydration, pH, and temperatures, and solution content (e.g., amount of stabilizer, sugar, etc.) has been characterized. These studies led to the characterization of the stability of rAAV over time in a dehydrated state. rAAV produced using the most commonly-utilized viral capsid structure (AAV serotype 2) was found to maintain transduction potential following desiccation. rAAVs produced using serotype 1, 3, 4, and 5 capsids were also found to maintain the potential for gene delivery following desiccation.

The present invention provides the ability to deliver genes via the dehydrated virus when applied to various suture materials (silk, cat gut, vicryl monofilament, and the like), to positively charged nylon membranes, to a foam gelatin matrix, and to polytetrafluoroethylene (PTFE) graft materials. Gene delivery and protein expression have been demonstrated using each of these materials in vitro and in vivo.

BRIEF DESCRIPTION OF THE DRAWINGS

As shown in FIG. 1C, the percentage of hematocrit in a mouse intramuscularly injected with a viral vector carrying EPO is lower over time than the percentage of hematocrit in a mouse treated with sutures comprising a viral vector carrying EPO.

DESCRIPTION OF THE PREFERRED EMBODIMENTS

Figure 1A:
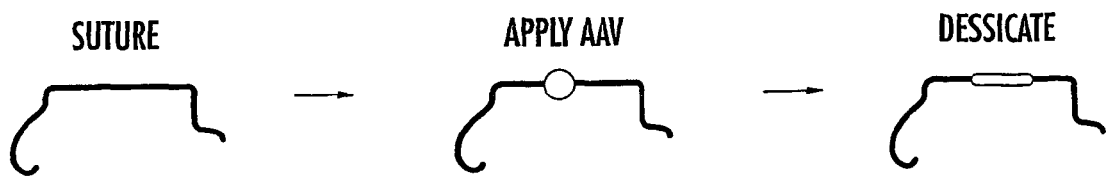
FIG. 1A is a schematic illustrating the basic method of the present invention. A surgically implantable matrix such as a suture is contacted with an AAV vector, preferably an rAAV vector comprising a heterologous nucleic acid. The vector is then dried (i.e, dessicated) onto the surgically implantable matrix.
Figure 1B:
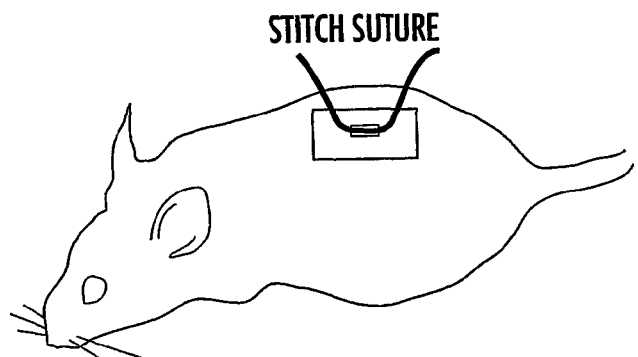
As illustrated in FIG. 1B, the matrix comprising the desiccated AAV vector is then implanted or stitched into or onto a subject (e.g, a human or a non-human animal), preferably such that the matrix material is absorbed into the subjects' body.
Figure 1C:
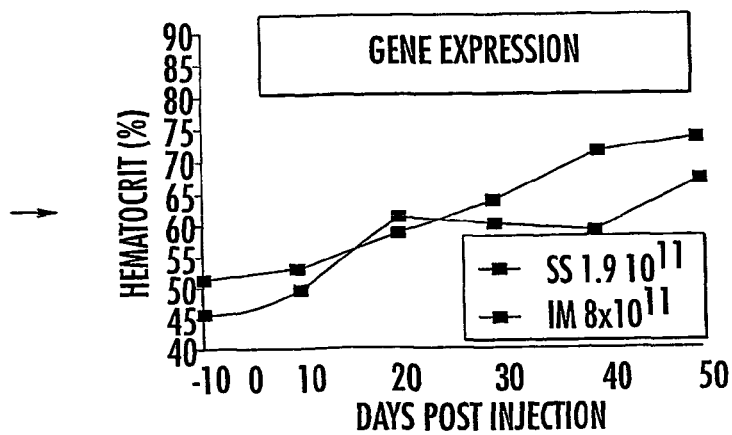
FIG. 1C is a graph illustrating that the percentage of hematocrit in a mouse intramuscularly injected with a viral vector carrying erythropoietin (EPO) is lower over time than the percentage of hematocrit in a mouse treated with sutures comprising the viral vector carrying EPO.

The present invention will now be described more fully hereinafter with reference to the accompanying drawings and specification, in which preferred embodiments of the invention are shown. This invention may, however, be embodied in different forms and should not be construed as limited to the embodiments set forth herein.

Unless otherwise defined, all technical and scientific terms used herein have the same meaning as commonly understood by one of ordinary skill in the art to which this invention belongs. As used in the description of the invention and the appended claims, the singular forms "a", "an" and "the" are intended to include the plural forms as well, unless the context clearly indicates otherwise. All publications, patent applications, patents, and other references mentioned herein are incorporated by reference in their entirety.

Except as otherwise indicated, standard methods known to those skilled in the art may be used for the construction of rAAV genomes, transcomplementing packaging vectors, and transiently and stably transfected packaging cells for use in the present invention. Such techniques are known: to those skilled in the art. See e.g., J. Sambrook et al., *Molecular Cloning: A Laboratory Manual Second Edition* (Cold Spring Harbor Laboratory, Cold Spring Harbor, N.Y., 1989), and F. M. Ausubel et al., *Current Protocols In Molecular Biology* (Green Publishing Associates, Inc. and Wiley-Interscience, New York, 1991).

Parvoviruses are relatively small DNA animal viruses that comprise a linear, single-stranded DNA genome. The term "parvovirus" as used herein encompasses the family Parvoviridae, including autonomously-replicating parvoviruses and dependoviruses. The autonomous parvoviruses include members of the genera Parvovirus, Erythrovirus, Densovirus, Iteravirus, and Contravirus. The autonomous parvoviruses include members of the genera Parvovirus, Erythrovirus, Densovirus, Iteravirus, and Contravirus. Exemplary autonomous parvoviruses include, but are not limited to, mouse minute virus, bovine parvovirus, canine parvovirus, chicken parvovirus, feline panleukopenia virus, feline parvovirus, goose parvovirus, and B19 virus. Other autonomous parvoviruses are known to those skilled in the art. See, e.g., K. I. Berns et al., "Parvoviridae: The Viruses And Their Replication," in *Virology, Third Edition* (B. N. Fields et al., eds., Lippincott-Raven, Philadelphia, Pa., 1996, pp. 2173–2197).

Within the Parvovirus family, the genus Dependovirus contains the adeno-associated viruses (AAV). Adeno-associated virus (AAV) is a nonpathogenic, helper-dependent member of the parvovirus family. The adeno-associated viruses include, but are not limited to, AAV type 1, AAV type 2, AAV type 3, AAV type 4, AAV type 5, AAV type 6, avian AAV, bovine AAV, canine AAV, equine AAV, and ovine AAV. In the use of the present invention, AAV type 1, AAV type 2, AAV type 3, AAV type 4, AAV type 5 are preferred, with AAV type 2 being particularly preferred.

Among the identifying characteristics of this group of viruses is a single-stranded DNA genome. In the case of AAV, either the plus or minus polarity strand can be packaged with equal efficiency, and both are infectious. Adeno-associated viruses generally require a helper virus for a productive infection. Although adenovirus (Ad) usually serves this purpose, treatment of AAV infected cells with UV irradiation or hydroxyurea will also allow limited replication.

Recombinant AAV (rAAV) gene delivery vectors are also packaged as single-strands of plus or minus polarity, and must rely on cellular replication factors for synthesis of the complementary strand. While it was originally expected that this step would be carried out spontaneously by cellular DNA repair synthesis pathways, this view now appears to be over-simplified. Early work with rAAV vectors in cultured cells revealed that the ability to score marker gene expression was dramatically enhanced when the cells were co-infected with adenovirus. This effect was observed in the absence of any AAV viral gene or known AAV cis-acting transcriptional regulatory sequences. Two groups subsequently demonstrated that the enhancement effect could be achieved through the expression of the Ad E4orf6 gene. Similar enhancement was observed when cells were treated with UV irradiation or other types of cell stress. Further, the dosage of these treatments correlated with the level of enhancement, which also correlated with the conversion of the single-stranded virion DNA (vDNA) genome into duplex. Similar induction of rAAV vectors has also been observed in vivo following treatment with Ad, UV, ionizing radiation, or topoisomerase inhibitors. However, the effect was highly variable between different tissues. More importantly, AAV vectors in vivo have been defined as requiring one to two weeks before optimum levels of transgene expression can be observed, a feature ascribed to second-strand synthesis See, e.g., Samulski et al., "Adeno-associated Viral Vectors," in *The Development of Human Gene Therapy* (T. Friedmann, ed., Cold Spring Harbor Laboratory Press, Cold Spring Harbor, N.Y., 1999).

The genomic sequences of various autonomous parvoviruses and the different serotypes of AAV, as well as the sequences of the TRs, capsid subunits, and Rep proteins are known in the art. Such sequences may be found in the literature or in public databases such as GenBank. See, e.g., GenBank Accession Numbers NC 002077, NC 001863, NC 001862, NC 001829, NC 001729, NC 001701, NC 001510, NC 001401, AF063497, U89790, AF043303, AF028705, AF028704, J02275, J01901, J02275, X01457, AF288061, AH009962, AY028226, AY028223, NC 001358, NC 001540; the disclosures of which are incorporated herein in their entirety. See also, e.g., Chiorini et al., (1999) *J. Virology* 73:1309; Xiao et al., (1999) *J. Virology* 73:3994; Muramatsu et al., (1996) *Virology* 221:208; international patent publications WO 00/28061, WO 99/61601, WO 98/11244; U.S. Pat. No. 6,156,303; the disclosures of which are incorporated herein in their entirety. An early description of the AAV1, AAV2 and AAV3 TR sequences is provided by Xiao, X., (1996), "Characterization of Adeno-associated virus (AAV) DNA replication and integration," Ph.D. Dissertation, University of Pittsburgh, Pittsburgh, Pa. (incorporated herein it its entirety).

Preferably, the rAAV genome comprises (i.e., "carries") a heterologous nucleic acid sequence, such as a DNA sequence or a gene. Any heterologous nucleotide sequence(s) may be delivered according to the present invention. Nucleic acids of interest include nucleic acids encoding peptides and proteins, preferably therapeutic (e.g., for medical or veterinary uses) or immunogenic (e.g., for vaccines) peptides or proteins.

As used herein, the term "vector" or "gene delivery vector" may refer to a parvovirus (e.g., AAV) particle that functions as a gene delivery vehicle, and which comprises vDNA (i.e., the vector genome) packaged within a parvovirus (e.g., AAV) capsid. Alternatively, in some contexts, the term "vector" may be used to refer to the vector genome/vDNA.

A "heterologous nucleotide sequence" will typically be a sequence that is not naturally occurring in the virus. Alternatively, a heterologous nucleotide sequence may refer to a viral sequence that is placed into a non-naturally occurring environment (e.g., by association with a promoter with which it is not naturally associated in the virus).

As used herein, a "recombinant parvovirus vector genome" is a parvovirus genome.(ie., vDNA) into which a heterologous (e.g., foreign) nucleotide sequence (e.g., transgene) has been inserted. A "recombinant parvovirus particle" comprises a recombinant parvovirus vector genome packaged within a parvovirus capsid.

Likewise, a "rAAV vector genome" is an AAV genome (i.e., vDNA) that comprises a heterologous nucleotide sequence. rAAV vectors require only the 145 base terminal repeats in cis to generate virus. All other viral sequences are dispensable and may be supplied in trans (Muzyczka, (1992) *Curr. Topics Microbiol. Immunol.* 158:97). Typically, the rAAV vector genome will only retain the minimal terminal repeat (TR) sequences so as to maximize the size of the transgene that can be efficiently packaged by the vector. A "rAAV particle" comprises a rAAV vector genome packaged within an AAV capsid.

Parvovirus particles of the present invention may be "hybrid" particles in which the viral TRs and viral capsid are from different parvoviruses. Preferably, the viral TRs and capsid are from different serotypes of AAV (e.g., as described in international patent publication WO 00/28004, U.S. Provisional Application No. 60/248,920; U.S. patent application Ser. No. 09/438,268 to Rabinowitz et al., and Chao et al., (2000) *Molecular Therapy* 2:619; the disclosures of which are incorporated herein in their entireties). Likewise, the parvovirus may have a "chimeric" capsid (e.g., containing sequences from different parvoviruses, preferably different AAV serotypes) or a "targeted" capsid (e.g., a directed tropism) as described in international patent publication WO 00/28004.

As used herein, a "parvovirus particle" encompasses hybrid, chimeric and targeted virus particles. Preferably, the parvovirus particle has an AAV capsid, which may further be a chimeric or targeted capsid, as described above.

As used herein, the term "polypeptide" encompasses both peptides and proteins, unless indicated otherwise.

As used herein, "transduction" or "infection" of a cell by AAV means that the AAV enters the cell to establish a latent or active (i.e., lytic) infection, respectively. See, e.g., *Virology, Third Edition* (B. N. Fields et al., eds., Lippincott-Raven, Philadelphia, Pa., 1996, pp. 2173–2197). In embodiments of the invention in which a rAAV vector is introduced into a cell for the purpose of delivering a nucleotide sequence to the cell, it is preferred that the AAV integrates into the genome and establishes a latent infection.

The viral capsid may be from any parvovirus, either an autonomous parvovirus or dependovirus, as described above. Preferably, the viral capsid is an AAV capsid (e.g., AAV1, AAV2, AAV3, AAV4, AAV5 or AAV6 capsid). In general, the AAV1 capsid, AAV5 capsid, and AAV3 capsid are preferred. The choice of parvovirus capsid may be based on a number of considerations as known in the art, e.g., the target cell type, the desired level of expression, the nature of the heterologous nucleotide sequence to be expressed, issues related to viral production, and the like. For example, the AAV1 capsid may be advantageously employed for skeletal muscle, liver and cells of the central nervous system (e.g., brain); AAV5 for cells in the airway and lung; AAV3 for bone marrow cells; and AAV4 for particular cells in the brain (e.g., appendable cells).

In preferred embodiments, the parvovirus vector further comprises a heterologous nucleotide sequence(s) (as described below) to be packaged for delivery to a target cell. According to this particular embodiment, the heterologous nucleotide sequence is located between the viral TRs at either end of the substrate. In further preferred embodiments, the parvovirus (e.g., AAV) cap genes and parvovirus (e.g., AAV) rep genes are deleted from the vector. This configuration maximizes the size of the heterologous nucleic acid sequence(s) that can be carried by the parvovirus capsid.

Preferably, the heterologous nucleotide sequence or sequences will be less than about 5.0 kb in length (more preferably less than about 4.8 kb, still more preferably less than about 4.4 kb, yet more preferably less than about 4.0 kb in length) to facilitate packaging by the AAV capsid. Exemplary nucleotide sequences encode Factor IX, erythropoietin, superoxide dismutase, globin, leptin, thymidine kinase, catalase, tyrosine hydroxylase, as well as cytokines (e.g., α-interferon, β-interferon, interferon-γ, interleukin-2, interleukin-4, interleukin 12, granulocyte-macrophage colony stimulating factor, lymphotoxin, and the like), peptide growth factors and hormones (e.g., somatotropin, insulin, insulin-like growth factors 1 and 2, platelet derived growth factor, epidermal growth factor, fibroblast growth factor, nerve growth factor, neurotrophic factor -3 and -4, brain-derived neurotrophic factor, glial derived growth factor, transforming growth factor-α and -β, and the like).

The present invention may also be used to deliver vectors for the purpose of expressing an immunogenic peptide or protein in a subject, e.g., for vaccination. The vectors will preferably comprise nucleic acid encoding any immunogen of interest known in the art including, but are not limited to, immunogens from human immunodeficiency virus, influenza virus, gag proteins, tumor antigens, cancer antigens, bacterial antigens, viral antigens, and the like.

As a further alternative, the heterologous nucleic acid sequence may encode a reporter polypeptide (e.g., an enzyme such as Green Fluorescent Protein, alkaline phosphatase).

Alternatively, in particular embodiments of the invention, the nucleic acid of interest may encode an antisense nucleic acid, a ribozyme (e.g., as described in U.S. Pat. No. 5,877,022), RNAs that effect spliceosome-mediated trans-splicing (see, Puttaraju et al., (1999) Nature Biotech. 17:246; U.S. Pat. No. 6,013,487; U.S. Pat. No. 6,083,702), interfering RNAs (RNAi) that mediate gene silencing (see, Sharp et al., (2000) Science 287:2431) or other non-translated RNAs, such as "guide" RNAs (Gorman et al., (1998) Proc. Nat. Acad. Sci. USA 95:4929; U.S. Pat. No. 5,869,248 to Yuan et al.), and the like.

The heterologous nucleic acid may be operably associated with expression control elements, such as transcription/translation control signals, origins of replication, polyadenylation signals, and internal ribosome entry sites (IRES), promoters, enhancers, and the like. Those skilled in the art will appreciate that a variety of promoter/enhancer elements may be used depending on the level and tissue-specific expression desired. The promoter/enhancer may be constitutive or inducible, depending on the pattern of expression desired. The promoter/enhancer may be native or foreign and can be a natural or a synthetic sequence.

Promoters/enhancers that are native to the subject to be treated are most preferred. Also preferred are promoters/ enhancers that are native to the heterologous nucleic acid sequence. The promoter/enhancer is chosen so that it will function in the target cell(s) of interest. Mammalian promoters/enhancers are also preferred.

Inducible expression control elements are preferred in those applications in which it is desirable to provide regulation over expression of the heterologous nucleic acid sequence(s). Inducible promoters/enhancer elements for gene delivery are preferably tissue-specific promoter/enhancer elements, and include muscle specific (including cardiac, skeletal and/or smooth muscle), neural tissue specific (including brain-specific), liver specific, bone marrow specific, pancreatic specific, spleen specific, retinal specific, and lung specific promoter/enhancer elements. Other inducible promoter/enhancer elements include hormone-inducible and metal-inducible elements. Exemplary inducible promoters/enhancer elements include, but are not limited to, a tet on/off element, a RU486-inducible promoter, an ecdysone-inducible promoter, a rapamycin-inducible promoter, and a metalothionein promoter.

In embodiments of the invention in which the heterologous nucleic acid sequence(s) will be transcribed and then translated in the target cells, specific initiation signals are generally required for efficient translation of inserted protein coding sequences. These exogenous translational control sequences, which may include the ATG initiation codon and adjacent sequences, can be of a variety of origins, both natural and synthetic.

The vector may contain some or all of the parvovirus (e.g., AAV) cap and rep genes. Preferably, however, some or all of the cap and rep functions are provided in trans by introducing a packaging vector(s) encoding the capsid and/ or Rep proteins into the cell. Most preferably, the vector does not encode the capsid or Rep proteins. Alternatively, a packaging cell line is used that is stably transformed to express the cap and/or rep genes (see, e.g., Gao et al., (1998) Human Gene Therapy 9:2353; Inoue et a., (1998) J. Virol. 72:7024; U.S. Pat. No. 5,837,484; WO 98/27207; U.S. Pat. No. 5,658,785; WO 96/17947).

A "therapeutic polypeptide" is a polypeptide that may alleviate or reduce symptoms that result from an absence or defect in a protein in a cell or subject. Alternatively, a "therapeutic polypeptide" is one that otherwise confers a benefit to a subject, e.g., anti-cancer effects or improvement in transplant survivability.

The parvovirus vector may also encode a heterologous nucleotide sequence that shares homology with and recombines with a locus on the host chromosome. This approach may be utilized to correct a genetic defect in the host cell.

The present invention may also be used to express an immunogenic polypeptide in a subject, e.g., for vaccination. The nucleic acid may encode any immunogen of interest known in the art including, but are not limited to, immunogens from human immunodeficiency virus, influenza virus, gag proteins, tumor antigens, cancer antigens, bacterial antigens, viral antigens, and the like.

The use of parvoviruses as vaccines is known in the art (see, e.g., Miyamura et al, (1994) Proc. Nat Acad. Sci USA 91:8507; U.S. Pat. No. 5,916,563 to Young et al., U.S. Pat. No. 5,905,040 to Mazzara et a., U.S. Pat. No. 5,882,652, U.S. Pat. No. 5,863,541 to Samulski et al.; the disclosures of which are incorporated herein in their entirety by reference). The antigen may be presented in the parvovirus capsid. Alternatively, the antigen may be expressed from a heterologous nucleic acid introduced into a recombinant vector genome. Any immunogen of interest may be provided by the parvovirus vector. Immunogens of interest are well-known in the art and include, but are not limited to, immunogens from human immunodeficiency virus, influenza virus, gag proteins, tumor antigens, cancer antigens, bacterial antigens, viral antigens, and the like.

An immunogenic polypeptide, or immunogen, may be any polypeptide suitable for protecting the subject against a disease, including but not limited to microbial, bacterial, protozoal, parasitic, and viral diseases. For example, the immunogen may be an orthomyxovirus immunogen (e.g., an influenza virus immunogen, such as the influenza virus hemagglutinin (HA) surface protein or the influenza virus nucleoprotein gene, or an equine influenza virus immunogen), or a lentivirus immunogen (e.g., an equine infectious anemia virus immunogen, a Simian Immunodeficiency Virus (SIV) immunogen, or a Human Immunodeficiency Virus (HIV) immunogen, such as the HIV or SIV envelope GP160 protein, the HIV or SIV matrix/capsid proteins, and the HIV or SIV gag, pol and env genes products). The immunogen may also be an arenavirus immunogen (e.g., Lassa fever virus immunogen, such as the Lassa fever virus nucleocapsid protein gene and the Lassa fever envelope glycoprotein gene), a poxyirus immunogen (e.g., vaccinia, such as the vaccinia L1 or L8 genes), a flavivirus immunogen (e.g., a yellow fever virus immunogen or a Japanese encephalitis virus immurogen), a filovirus immunogen (e.g., an Ebola virus immunogen, or a Marburg virus immunogen, such as NP and GP genes), a bunyavirus immunogen (e.g., RVFV, CCHF, and SFS viruses), or a coronavirus immunogen (e.g., an infectious human coronavirus immunogen, such as the human coronavirus envelope glycoprotein gene, or a porcine transmissible gastroenteritis virus immunogen, or an avian infectious bronchitis virus immunogen). The immunogen may further be a polio immunogen, herpes antigen (e.g., CAAV, EBV, HSV immunogens) mumps immunogen, measles immunogen, rubella immunogen, diptheria toxin or other diptheria immunogen, pertussis antigen, hepatitis (e.g., hepatitis A or hepatitis B) immunogen, or any other vaccine immunogen known in the art.

Alternatively, the immunogen may be any tumor or cancer cell antigen. Preferably, the tumor or cancer antigen is expressed on the surface of the cancer cell. Exemplary cancer and tumor cell antigens are described in S.A. Rosenberg, (1999) *Immunity* 10:281). Other illustrative cancer and tumor antigens include, but are not limited to: BRCAI gene product, BRCA2 gene product, gp100, tyrosinase, GAGE-½, BAGE, RAGE, NY-ESO-1, CDK4, β-catenin, MUM-1, Caspase-8, KIAA0205, HPVE, SART-1, PRAME, p15, melanoma tumor antigens (Kawakami et al., (1994) *Proc. Natl. Acad. Sci. USA* 91:3515); Kawakami et al., (1994) *J. Exp. Med.*, 180:347); Kawakami et al., (1994) *Cancer Res.* 54:3124), including MART-1 (Coulie et al., (1991) *J. Exp. Med.* 180:35), gp100 (Wick et al., (1988) *J. Cutan. Pathol.* 4:201) and MAGE antigen, MAGE-1, MAGE-2 and MAGE-3 (Van der Bruggen et al., (1991) *Science*, 254:1643); CEA, TRP-1, TRP-2, P-15 and tyrosinase (Brichard et al., (1993) *J. Exp. Med.* 178:489); HER-2/neu gene product (U.S. Pat. No. 4,968,603), CA 125, LK26, FB5 (endosialin), TAG 72, AFP, CA19-9, NSE, DU-PAN-2, CA50, SPan-1, CA724, HCG, STN (sialyl Tn antigen), cerbB-2 proteins, PSA, L-CanAg, estrogen receptor, milk fat globulin, p53 tumor suppressor protein (Levine, (1993) *Ann. Rev. Biochem.* 62:623); mucin antigens (international patent publication WO 90/05142); telomerases; nuclear matrix proteins; prostatic acid phosphatase; papilloma virus antigens; and antigens associated with the following cancers: melanomas, metastases, adenocarcinoma, thymoma, lymphoma, sarcoma, lung cancer, liver cancer, colon cancer, non-Hodgkins lymphoma, Hodgkins lymphoma, leukemias, uterine cancer, breast cancer, prostate cancer, ovarian cancer, cervical cancer, bladder cancer, kidney cancer, pancreatic cancer and others (see, e.g., Rosenberg, (1996) *Ann. Rev. Med.* 47:481–91).

Accordingly, the present invention finds use in methods of treating cancer or tumors, e.g., by delivery of anti-cancer agents or cancer antigens. In particular embodiments, the inventive methods are used to administer anticancer agents or cancer antigens to prevent metastasis, e.g., following surgical removal of a primary tumor.

The inventive methods and matrices may also advantageously be used in the treatment of individuals with metabolic disorders (e.g., omithine transcarbamylase deficiency). Such disorders typically require a relatively rapid onset of expression of a therapeutic polypeptide by the gene delivery vector. As still a further alternative, the inventive vectors may be administered to provide agents that improve transplant survivability (e.g., superoxide dismutase) or combat sepsis.

rAAV vectors of the present invention are applied for delivery onto surgically implantable matrices as described herein. In the method of the present invention, rAAV vectors in solution are contacted with surgically implantable matrices or materials and allowed to dry or dehydrate onto or into the surgically implantable materials or matrices. The vectors in solution may be contacted with the implantable matrices or materials by submerging or immersing the matrices or materials in the solution. Alternatively, the vectors in solution may be contacted with the implantable matrices in a drop-wise manner, or may be sprayed onto the implantable matrices, or otherwise contacted with the matrices using methods that will be easily determined by those skilled in the art.

Figure 6:
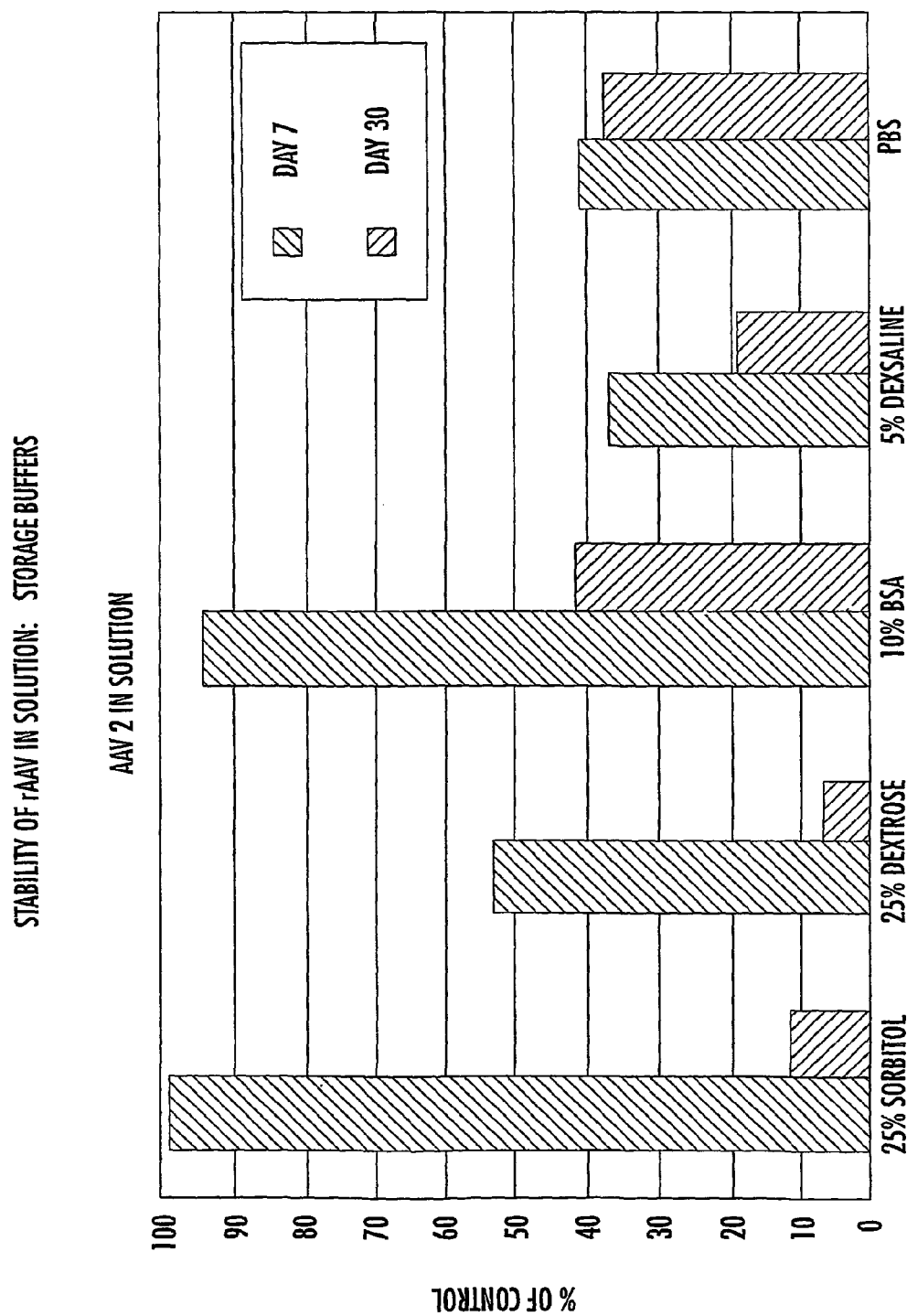
FIG. 6 is a graphical illustration comparing the effect on rAAV Type 2 stability of storage solutions comprising different stabilizers in varying concentrations.

In a preferred embodiment of the invention, prior to drying/desiccation, the parvovirus (e.g., rAAV) vectors are in a solution and/or maintained in a solution (e.g., a storage solution) comprising a stabilizer. In other words, in a preferred embodiment, rAAV vectors are in a stabilizer-containing solution when they are desiccated. It has been unexpectedly discovered by the present inventors that rAAV vectors in solutions comprising at least one stabilizer are more stable after desiccation and rehydration/resuspension. Moreover, post-desiccation, the rAAV vectors originally desiccated from a solution comprising a stabilizer have a higher transduction efficiency when compared to those vectors that were not desiccated from solution comprising a stabilizer (e.g., as compared to virus in PBS buffer only). Preferred stabilizers are sugars and sugar alcohols; more preferred stabilizers are sorbitol, sucrose, and dextrose, with sorbitol being particularly preferred. In preferred embodiments, the stabilizer (e.g., sorbitol), comprises at least about 5% of the solution (e.g., is a 5% sorbitol solution); more preferably at least about 10% of the solution, even more preferably at least about 15%, still more preferably 20%, and in a most particularly preferred embodiment, at least 25%. In one preferred embodiment, the storage solution comprising the vector/virus comprises 25% sorbitol. FIG. 6 graphically illustrates the comparison of storage solutions comprising different stabilizers in varying concentrations; the comparison is expressed in terms of the stability of rAAV 2 vectors (as a percentage of control vectors) seven days after gene delivery and thirty days after gene delivery of the dried vector.

The drying or dehydrating step may be carried out according to known techniques (desiccation, desiccation under vacuum conditions, lyophilization, evaporation, etc.). Desication or drying is preferably complete (i.e., at or approaching 0% solution or water), but alternatively may be partial.

Surgically implantable matrices or materials are those materials that may be inserted, implanted, sewn into, or otherwise contacted with the cells, and/or tissues, and/or body of a subject, internally or externally. Surgically implantable matrices or materials or the present invention may be porous or non-porous, flexible or non-flexible, weaved or non-weaved, absorbable or non-absorbable.

Preferably, the surgically implantable matrix is absorbable; that is, the matrix is absorbed into the body of the subject over time. Such matrices include sutures, surgically implantable devices and materials, and graft materials. If absorption of the material and/or the rAAV vector is desired, the time or rate of absorption can be controlled by selection of material, by the dosage of the virus, location of the implantable material, etc. Sutures used in the present invention may be sewn onto or into skin, muscle, peritoneum or other surfaces in or on the subjects' body. Surgically implantable materials (grafts, sutures, etc.) particularly useful in the present invention include vicryl and monocryl (available from Ethicon, a subsidiary of Johnson and Johnson), Nytran™ (nylon), Gortex® (polytetrafluoroethylene or "PTFE"), Marlex® (crystalline polypropylene and high-density polyethylene [HDPE]), polypropylene, cat gut (chromic, about one to two weeks, until absorbed into the body), polygalactin (three to four weeks for absorption), PDS (about six weeks for absorption), and Dacron® (polyester fiber), with cat gut and Gortex® being presently preferred.

In one embodiment of the invention, the surgically implantable material is coated. Suitable coating materials are known in the art and include collagen and glutaraldehyde-linked collagen. Another strategy that has been used with grafts to be used inside blood vessels (where the development of fibrosis at the foreign implanted material is not desired) is to bond heparin to the graft material that is released slowly over the first few weeks after the graft is implanted goes in. Albumin coatings have also been used, as well as certain coating gels known in the art. In one alternative embodiment of the invention, heparin is used to coat the surgically implantable material and used to "hold" or bind the rAAV to the implantable material (see U.S. patent application Ser. No. 09/228,203 to Samulski et al., the disclosure of which is incorporated herein by reference in its entirety). The rAAV may then be released from the implanted material by exchanging it with cellular receptors as the heparin is absorbed from the graft.

In other embodiments of the invention, helper virus functions are optionally provided for the parvovirus vector, preferably at the site of delivery. In a preferred embodiment, the target tissue or cell of the gene delivery is treated with a helper function (i.e., is treated with a solution of helper virus) prior to the implantation of the rAAV/surgical matrix of the present invention. Both adenovirus and herpes simplex virus may serve as helper viruses for AAV. See, e.g., Bernard N. Fields et al., Virology, volume 2, chapter 69 (3d ed., Lippincott-Raven Publishers). Exemplary helper viruses include, but are not limited to, Herpes simplex (HSV) varicella zoster, cytomegalovirus, and Epstein-Barr virus. The multiplicity of infection (MOI) and the duration of the infection will depend on the type of virus used and the packaging cell line employed. Any suitable helper vector may be employed. Preferably, the helper vector(s) is a plasmid, for example, as described by Xiao et al., (1998) *J.* *Virology* 72:2224. The vector can be introduced into the packaging cell by any suitable method known in the art, as described above.

A preferred method for providing helper functions employs a noninfectious adenovirus miniplasmid that carries all of the helper genes required for efficient AAV production (Ferrari et al., (1997) *Nature Med.* 3:1295; Xiao et al., (1998) *J. Virology* 72:2224). The rAAV titers obtained with adenovirus miniplasmids are forty-fold higher than those obtained with conventional methods of wild-type adenovirus infection (Xiao et al., (1998) *J. Virology* 72:2224). This approach obviates the need to perform co-transfections with adenovirus (Holscher et al., (1994), *J. Virology* 68:7169; Clark et al, (1995) *Hum. Gene Ther.* 6:1329; Trempe and Yang, (1993), in, Fifth Parvovirus Workshop, Crystal River, FL).

Herpesvirus may also be used as a helper virus for AAV. Hybrid herpesviruses encoding the AAV Rep protein(s) may advantageously facilitate for more scalable AAV vector production schemes. A hybrid herpes simples virus type I (HSV-1) vector expressing the AAV-2 rep and cap genes has been described (Conway et al., (1999) *Gene Therapy* 6:986 and WO 00/17377, the disclosures of which are incorporated herein in their entireties).

In view of the foregoing, the present invention is useful in delivering genes and other nucleic acid sequences either in vitro (to cells) or in vivo (to subjects) by contacting cells, tissues or subjects' bodies to surgically implantable material treated with rAAV. Suitable subjects include both avians and mammals, with mammals being preferred. The term "avian" as used herein includes, but is not limited to, chickens, ducks, geese, quail, turkeys and pheasants. The term "mammal" as used herein includes, but is not limited to, humans, bovines, ovines, caprines, equines, felines, canines, lagomorphs, etc. Human subjects are the most preferred. Human subjects include fetal, neonatal, infant, juvenile and adult subjects.

Recombinant virus vectors are preferably delivered to a target tissue in a biologically-effective amount. A "biologically-effective" amount of the virus vector is an amount that is sufficient to result in infection (or transduction) and expression of the heterologous nucleic acid sequence in the target tissue. If the virus is administered in vivo (e.g., the virus is administered to a subject as described below), a "biologically-effective" amount of the virus vector is an amount that is sufficient to result in transduction and expression of the heterologous nucleic acid sequence in a target cell.

The parvovirus vector administered to the subject may transduce any permissive cell or tissue. Suitable cells for transduction by the inventive parvovirus vectors include but are not limited to: neural cells (including cells of the peripheral and central nervous systems, in particular, brain cells), lung cells, retinal cells, epithelial cells (e.g., gut and respiratory epithelial cells), muscle cells, dendritic cells, pancreatic cells (including islet cells), hepatic cells, myocardial cells, bone cells (e.g., bone marrow stem cells), hematopoietic stem cells, spleen cells, keratinocytes, fibroblasts, endothelial cells, prostate cells, germ cells, and the like. Alternatively, the cell may be any progenitor cell. As a further alternative, the cell can be a stem cell (e.g., neural stem cell, liver stem cell). As still a further alternative, the cell may be a cancer or tumor cell. Moreover, the cells can be from any species of origin, as indicated above.

Dosages of the inventive parvovirus particles will depend upon the mode of administration, the disease or condition to be treated, the individual subject's condition, the particular virus vector, and the gene to be delivered, and can be determined in a routine manner. Exemplary doses for achieving therapeutic effects are virus titers of at least about $10^5$, $10^6$, $10^7$, $10^8$, $10^9$, $10^{10}$, $10^{11}$, $10^{12}$, $10^3$, $10^{14}$, $10^{15}$ transducing units or more, preferably about $10^8$–$10^{13}$ transducing units, yet more preferably $10^{12}$ transducing units.

The methods of the present invention also provide a means for delivering heterologous nucleotide sequences into a broad range of tissue, cells, including tissue comprising dividing and/or non-dividing cells. The present invention may be employed to deliver a nucleotide sequence of interest to a cell in vitro, e.g., to produce a polypeptide in vitro or for ex vivo gene therapy. The cells, pharmaceutical formulations, and methods of the present invention are additionally useful in a method of delivering a nucleotide sequence to a subject in need thereof, e.g., to express an immunogenic or therapeutic polypeptide. In this manner, the polypeptide may thus be produced in vivo in the subject. The subject may be in need of the polypeptide because the subject has a deficiency of the polypeptide, or because the production of the polypeptide in the subject may impart some therapeutic effect, as a method of treatment or otherwise, and as explained further below.

In general, the present invention may be employed to deliver any foreign nucleic acid with a biological effect to treat or ameliorate the symptoms associated with any disorder related to gene expression. Illustrative disease states include, but are not limited to: cystic fibrosis (and other diseases of the lung), hemophilia A, hemophilia B, thalassemia, anemia and other blood disorders, AIDS, Alzheimer's disease, Parkinson's disease, Huntington's disease, amyotrophic lateral sclerosis, epilepsy, and other neurological disorders, cancer, diabetes mellitus, muscular dystrophies (e.g., Duchenne, Becker), Gaucher's disease, Hurlers disease, adenosine deaminase deficiency, glycogen storage diseases and other metabolic defects, retinal degenerative diseases (and other diseases of the eye), diseases of solid organs (e.g., brain, liver, kidney, heart), and the like.

Gene transfer has substantial potential use in understanding and providing therapy for disease states. There are a number of inherited diseases in which defective genes are known and have been cloned. In general, the above disease states fall into two classes: deficiency states, usually of enzymes, which are generally inherited in a recessive manner, and unbalanced states, which may involve regulatory or structural proteins, and which are typically inherited in a dominant manner. For deficiency state diseases, gene transfer could be used to bring a normal gene into affected tissues for replacement therapy, as well as to create animal models for the disease using antisense mutations. For unbalanced disease states, gene transfer could be used to create a disease state in a model system, which could then be used in efforts to counteract the disease state. Thus the methods of the present invention permit the treatment of genetic diseases. As used herein, a disease state is treated by partially or wholly remedying the deficiency or imbalance that causes the disease or makes it more severe. The use of site-specific recombination of nucleic sequences to cause mutations or to correct defects is also possible.

The instant invention may also be employed to provide an antisense nucleic acid to a cell in vivo. Expression of the antisense nucleic acid in the target cell diminishes expression of a particular protein by the cell. Accordingly, antisense nucleic acids may be administered to decrease expression of a particular protein in a subject in need thereof.

The application of desiccation/drying of rAAV for packaging and transport and subsequent administration following reconstitution or delivery on an implantable physical matrix is applicable in a broad range of therapeutic situations. A clear application would be in vaccine development. rAAV vectors designed to provoke and maintain an immune response (and innate host immunity, e.g. versus hepatitis or immunodeficiency viruses) could be transported to developing countries and delivered to even remote areas without need for stringent preservation methods.

Additional embodiments and illustrations of the present invention include the following:

rAAV-impregnated Gortex® or other graft material may be overlaid directly on muscle or other tissue to deliver to large muscle mass over time. Other therapeutic strategies where this embodiment may be especially effective include transducing a large, thin muscle like the diaphragm, where penetrating a large surface area of tissue could make a dramatic difference in the pulmonary function, and using anti-cancer gene delivery locally following surgical debulking of a tumor to kill residual tumor in the surgical bed (e.g. with angiostatin/endostatin).

Moreover, a large bulk of muscle can be transduced from the vascular bed with a strategy involving either rAAV-impregnated vascular graft (or an rAAV vascular graft in combination with a bolus intra-vascular dose or viral vector). This embodiment involves isolating the artery that supplies, for example, the entire quadriceps muscle. Implanting an rAAV-impregnated graft into this artery causes virus to be released continuously into the entire end-capillary bed of the muscle, rather than simply the part of the muscle hit by an intramuscular injection or the surface that a graft lies on. This would be analogous to injection directly into the portal vein, but the dose would not necessarily be delivered all at once. In fact, the venous outflow of an individual limb could be occluded temporarily (for a half hour or longer) so that a bolus of virus could be delivered to saturate immediate binding followed by the longer-term release from the graft as it is absorbed or heals in.

The present method would also be useful in AAV transduction in vascular smooth muscle (i.e., coronary artery transduction/gancyclovir treatment for restenosis).

The present invention finds particular use in the application or administration of a known amount of rAAV virus as a film to permanent or absorbable matrix for gene delivery to wide surface areas through which dispersion would be difficult with injection methods. As an example, the human diaphragm muscle is several cell layers thick but a its total surface area is measured in square feet. Failure of the diaphragm muscle leads to the respiratory failure that ultimately contributes to death in the disease muscular dystrophy. An implantable matrix material, capable of rapid off-loading of AAV gene therapy vector (e.g. PTFE with a mini-dystrophin gene), could be applied to the diaphragm muscle, and lead to uniformity of transduction over a large surface area in a way that would be difficult to accomplish with multiple injections of gene therapy vector.

Similarly, sheets or films of rAAV may be directly and uniformly administered to flat or complex anatomic surfaces. For example, the present invention could be used to deliver rAAV vectors comprising or encoding antitumor agents directly into a tumor bed after complete or partial resection, to prevent local tumor recurrences. It has been demonstrated that a number of types of solid tumors will grow primarily at the site of original tumor, but following resection of the original tumor, distant sites of micrometastatic disease will appear. Any of a number of antineoplastic genes could be delivered this way, including gene for angiogenesis inhibitor agents (e.g. endostatin (preferred embodiment),angiostatin), for direct tumor antimetabolites, and for interleukins and other immune mediators to affect local or metastatic recurrence.

In another embodiment, the invention facilitates the delivery of growth factors onto absorbable or permanent tissue "scaffolds" in order to direct remodeling of bone or soft tissue. For example, rAAV vectors encoding genes for bone morphogenetic proteins (BMPs) or the upstream factors that mediate bone morphogenetic proteins could be stably immobilized onto biodegradable polymer scaffolds. The combined AAV virus/biomaterial can be used in a clinical setting as a bone-graft substitute to promote bone or ligament repair, as an osteo-inductive or chondrogenic mechanism. Synthetic materials that are currently used as structural support for new bone formation include polylactic acid homopolymers (PLA), plylactic acid-polyethylene glycol block copolymers (PLA-PEG), and polyglycolide (PGA). Candidate genes that could be delivered via immobilized stably desiccated rAAV include growth factors (transforming growth factor-beta1), bone morphogenetic proteins (BMPs). As new bone or ligament responds to the rAAV-delivered growth factor and infiltrates the scaffold, the scaffold can degrade and new bone or ligament has been stimulated by the viral gene therapy to grow into and repair the defect.

A similar strategy could be used to recruit and direct nerve regeneration. rAAV have already demonstrated the ability to deliver growth factors in the central nervous system (e.g. glial cell line-derived neurotrophic factor GDNF). This and other nerve growth factors NGFs could be localized to guide nerve regeneration by rAAV/NGFs that have been desiccated onto inert implantable materials, e.g. for spinal cord regeneration.

In yet another embodiment of the invention vascular graft materials (e.g., GoreTex®) that have rAAV gene therapy vectors on the surface or are impregnated with rAAV gene therapy vectors are developed. One problem of most vascular graft materials is that they tend to re-occlude due to ingrowth of endothelial cells (a process partially directed by angiogenic growth factors-preferred embodiment) and atherothrombotic processes. rAAV directing the expression of antisense oligonucleotides against vascular endothelial growth factors, focal adhesion kinase (FAK), or a variety of other factors may allow prolonged vascular patency following vascular graft placement, particularly if the gene delivery can be controlled to occur at a slow off-rate over time. One embodiment is a vascular graft material for arteriovenous hemodialysis shunts, formulated with an rAAV vector that inhibits loss of patency of the shunt and an additional rAAV-regulated erythropoietin vector that corrects the erythropoietin-deficient anemia of renal failure.

Alternatively, dried therapeutic rAAV may be formulated for slower release over time, following restoration of patency in coronary (heart) or peripheral blood vessels, delivering angiogenic growth factors to reverse impaired cardiomyopathy or peripheral myopathy. Gene delivery to blood vessels has been attempted using transient complete occlusion of blood vessels and infusion of gene therapy vector, with the time of exposure to the vector necessarily limited by the time the blood vessel can be blocked. The ability to deliver the rAAV itself dried on a vascular graft material with characterized properties of release of the virus advantageously circumvents this limitation.

Several embodiments are suggested by the demonstrated stability of the rAAV when dehydrated from solutions of 10–25% stabilizer (e.g., sorbitol), resulting in solid, buffered, sugar-based solid masses or "balls" of rAAV retaining transduction capability. For instance, it will be possible to make beads of rAAV for directed local delivery of therapy. For certain cancer treatment approaches, the present invention facilitates the release of rAAV from the sorbitol beads for more prolonged exposure to rAAV vector than can be achieved using direct injection. More prolonged exposure will result in contact with a greater proportion of cells that are cycling through the cell cycle, i.e. more cells that are susceptible to anti-neoplastic or suicide gene products. A strategy similar to the use of brachytherapy for intracavitary radiation therapy could be applied.

Patients with cervical cancer are often treated with brachytherapy, involving placement of afterloading applicators into the vaginal and uterine cavities and radiographic confirmation of proper placement of the applicators in proximity to the malignancy. Encapsulated radioactive sources are later inserted into the applicators, and deliver anatomically localized radiation therapy over time as the material (usually $^{137}$Cs or $^{226}$Ra) decays over days. Instead of radiation, very localized, dried rAAV "balls" or "beads" could be positioned in anatomic proximity to the lesion to deliver anticancer agents and/or achieve a "bystander" tumor kill that would not be feasible with simple injection of rAAV in solution. Such a strategy is feasible for a range of cancers (currently treated with radiation brachytherapy), including anal/rectal cancer, cervical carcinoma, endometrial carcinoma, vaginal cancer, pleural mesothelioma, nasopharyngeal carcinoma, and prostate cancer.

The demonstration of the stability of virus in the dried/desiccated state facilitates the delivery of molecular medicine, particularly in settings out side of tertiary care hospitals. The strategies developed for this application for stabilizing rAAV of serotypes 1, 2, 3, 4 and 5 can also be applied to so-called chimeric or hybrid capsid structure rAAV vectors (see U.S. patent application Ser. No. 09/438, 268, to Rabinowitz et al., incorporated herein by reference).

Currently, solutions of gene therapy vectors require careful storage conditions (generally requiring maintenance in frozen state at −20 or −80 degrees Celsius). The demonstration that rAAV vectors can maintain efficient transduction capability dried at room temperature makes feasible delivery of molecular medicine to geographically or technologically remote areas, including to developing countries. For instance, an analogous application has been the development earlier in this century of systems for maintaining viability of vaccines delivered to developing countries. This system has depended on establishing a "cold chain" of refrigeration, which in some countries with unreliable electricity has depended on kerosene or solar refrigeration. The establishment of efficacy of rAAV following room temperature storage in the dried state, with the capacity to manipulate controlled release, suggest the present inventive strategies will be critical to the wide-spread development of rAAV vaccines. rAAV vectors designed to provoke and maintain an immune response (and innate host immunity, e.g. versus hepatitis or humanimmunodeficiency viruses) could be transported to developing countries and delivered to even remote areas without need to stringent preservation methods.

In general, gene therapy holds promise for correction of disease states for which available therapy for symptomatic treatment exists, but is too costly for the majority of the world's population. For example, the average cost of treatment with coagulation factor IX or VII for U.S. hemophilic patients averages $50,000–$100,000 United States dollars per year. In underdeveloped countries, this cost precludes any treatment for most hemophilic patients, as does the need for refrigeration of treatment products. Recent pre-clinical and clinical trials with rAAV suggest that long-term correction of hemophilia with rAAV gene therapy will be achieved. The ability to prepare and transport rAAV as described by this invention suggest that the limitations to use of conventional therapy in underdeveloped countries could be overcome by the stability of the desiccated/implantable rAAV.

Although applications for vaccine development or for the host secretion of a therapeutic protein (as in correction of hemophilia) generally lead to a systemic effect, one advantage of the present invention is the ability to deliver genes locally (i.e., not systemically, but limited to a particular tissue, organ, area, etc.). For instance, following resection of a cancer of the type that is known to recur locally, a cancer-fighting rAAV (i.e., an rAAV vector comprising a nucleic acid encoding an anti-cancer compound) on an inert meshwork could be applied to the area of the tumor bed to prevent local recurrence, as an adjuvant therapy for surgery and chemotherapy. The localization of the therapy to the tumor bed and the potential local expression of cancer-fighting genes could be more specific than chemotherapy, which would either be administered systemically (with effects on the whole body) or would rapidly diffuse away after local administration. Diseases caused by protein deficiencies within specific tissue cell types, rather than by deficiencies of circulating proteins, could be targeted using an implanted matrix impregnated with the virus vector. For instance, delivery of the gene for dystrophin on a matrix applied directly to the diaphragm muscle could lead to improved pulmonary mechanics and decreased mortality in muscular dystrophy.

The following Examples are provided to illustrate the present invention, and should not be construed as limiting thereof.

EXAMPLE 1

Recombinant AAV2 produced using a triple transfection protocol, and expressing the gene for the green fluorescent protein (GFP), was applied to 3.0 vicryl suture material (Ethicon, Somerville, N.J.) or to a circle of positively charged nylon membrane (GeneScreen Plus, NEN Life Science, Boston,Mass.) and allowed to air dry in a room temperature vacuum. HeLa cells were grown to approximately 80–90% confluence in monolayer tissue culture were overlain with either the AAV/GFP/suture or the AAV/GFP/Nytran™ and allowed to infect for periods of time up to 30 minutes, prior to removal of the virus-impregnated material. Following overnight incubation, cells were examined for transduction with GFP by direct visualization of fluorescing cells using a Leitz DM IRB fluorescence microscopic (Leica, Heerbrugg, Switzerland).

Subsequently, rAAV/suture (coated 3-0 or 4-0 coated, braided polyglactin suture or 4-0 chromic gut suture) was prepared under sterile conditions in a negative pressure tissue culture hood by suspending 3.0 vicryl suture material (Ethicon, Somerville, N.J.) across the lip of autoclaved beaker and applying virus dropwise to the suture so that the exact titer of rAAV applied was known. Lengths of suture with known applied doses were then clipped and stored dry and sterile at room temperature for various lengths of time from days to months. At sequential timepoints, lengths of rAAV/suture encoding the gene lacZ were applied to 293 cells in tissue culture, which had previously undergone a one hour incubation with adenovirus type 2. Following a one hour infection with suture/rAAVlacZ, the suture was removed. On the following day, cells were stained for transduction and expression of lacZ, a marker gene that turns the cells blue under specific staining conditions. Suture that had been prepared and stored at room temperature as described did not lose appreciable transduction efficiency over the first week following preparation, and retained infectivity for at least three months.

EXAMPLE 2

In parallel to the experiments outlined in Example 1, Nytran® (positively charged nitrocellulose membrane) was investigated as a platform for virus. Uniform-sized circles of Nytran® were prepared and sterilized by autoclaving. Various doses of virus ($10^6$, $5\times10^5$, $10^5$, $5\times10^4$, $10^4$ and $5\times10^3$ transducing units) in a total volume of 10 ml were added to the membrane and dessicated in place under vacuum without heat. The underlining paper of the Nytran® disk was visibly wet by the virus in ten micro-liters. The Nytran® disks and the underlining paper were placed inverted on nearly confluent 293 cells, which were previously infected with Ad (4 hrs prior to the matrix/rAAV). The position of the disc on the plate was marked on the underside of the plate, and the disk removed after one hour infection. The next day, the plates of cells were stained for lacZ and the blue staining observed to occur primarily in the cells directly underlying the matrix/rAAV placement.

EXAMPLE 3

Each of the above experiments was repeated using rAAV/suture or rAAV/matrix carrying the gene for the marker green fluorescent protein (GFP) and performed on HeLa cells. Comparable results were obtained, with marker green fluorescence seen in cells that had been overlain with the virus-impregnated materials.

EXAMPLE 4

Initial attempts at in vivo application of the rAAV/GFP/suture technology were carried out in mouse muscle, but were limited by autofluorescence in mouse muscle that rendered any detection of GFP-mediated fluorescence above background fluorescence impossible. To prove the utility of the inventive approach with a physiologically important gene, recombinant AAV carrying the mouse gene for erythropoietin (rAAV/mEpo) was produced. Erythropoietin is normally secreted by the kidneys and directs the bone marrow to increase red blood cell production, reflected in an increase in the hematocrit (the percentage of blood volume occupied by red blood cells). rAAV/mEpo was produced using a triple plasmid transfection protocol which minimizes the contamination of the rAAV prep with helper adenovirus proteins. Virus was further purified by centrifugation on an iodixinol gradient and FPLC column purification on a heparin sulfate column. Following determination of rAAV vector genome titer by radioactive dot-blot assay, virus was dialyzed against sterile phosphate buffered saline (PBS) and diluted to a concentration of $8\times10^{11}$ vector genomes/ml (vg/ml). Separate sutures prepared using the technique described above (suspension of suture with known volumes of virus aliquoted to suture in drop-wise fashion) with the following doses:

$2.4\times10^{10}$ vg on single monofilament polyglactin (Monocryl® brand Ethicon suture)

$7.2\times10^{10}$ vg on single Monocryl suture $9.6\times10^{10}$ vg on single Monocryl suture 1.9×10¹¹ vg on single Monocryl suture 5×10¹¹ vg divided on one 5-0 chromic gut suture and one Monocryl suture Each suture was marked to delineate the length of suture on which the virus was located. Sutures were placed in a vacuum at low temperature with all virus being adsorbed within 24 hours.

EXAMPLE 5

Figure 2:
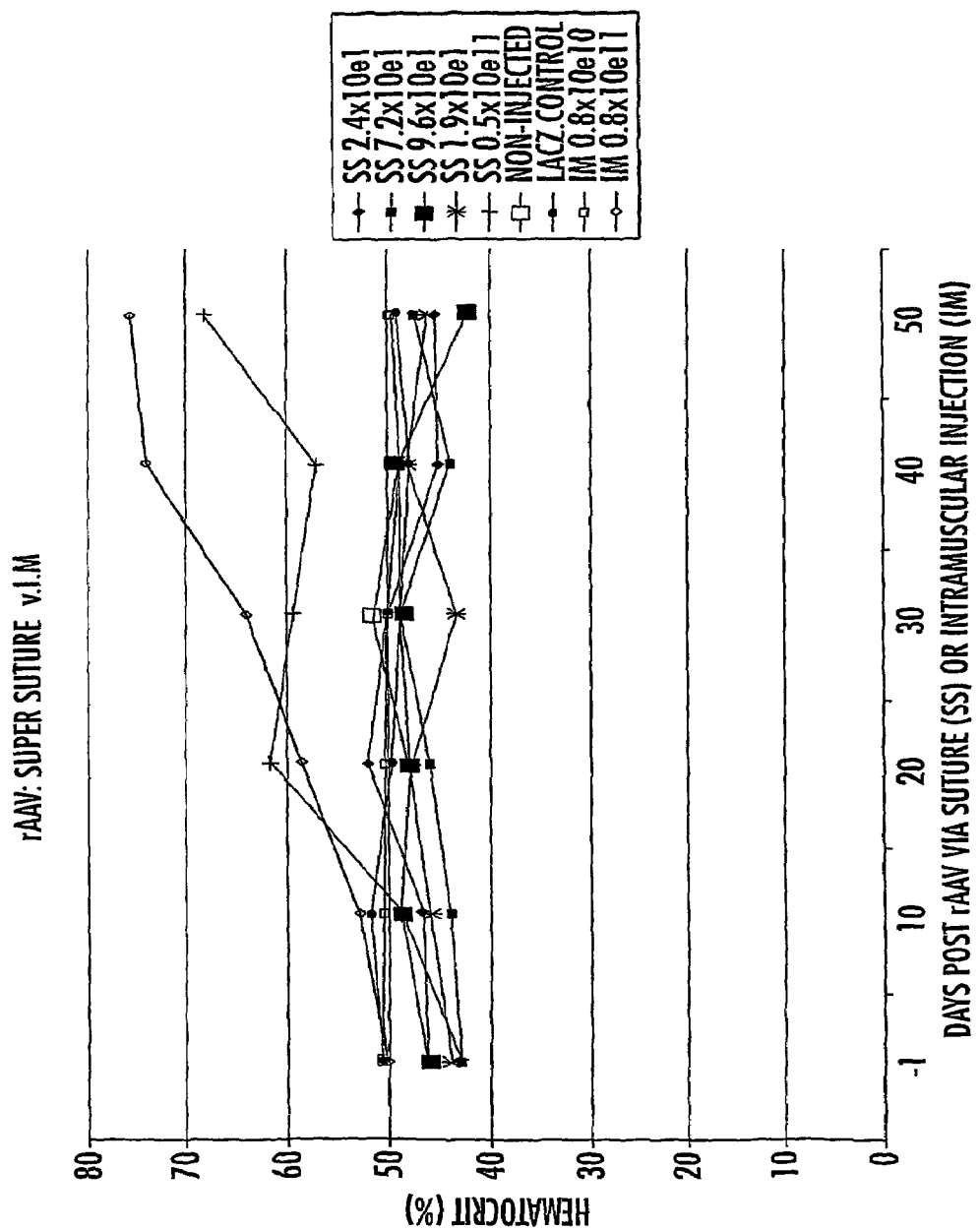
FIG. 2 is a graph of the embodiment of the invention described in Example 5 below. In this figure, "SS" mean "super suture," which is a suture material treated with rAAV vector carrying the EPO gene. The y-axis is labeled in terms of percentage hematocrit in the subject.(here, a mouse). The x-axis is labeled in terms of days after rAAV administration. The legend details which data points are from intramuscular injection of the rAAV vector carrying the EPO gene, and which are from sutures onto which rAAV vector carrying the EPO gene has been desiccated, and the dosage of vector administrated by each method.

Five 4 week-old BalbC mice had blood sampled to determine baseline normal hematocrit levels. Hematocrit levels in all four mice were between 43 and 46%, at baseline. Each mouse was anesthetized with intraperitoneal Avertin and an incision made to expose the quadriceps muscle of the leg. Suture was drawn through the muscle until the marker portion was positioned within the muscle bed, and tied in place. The edges of the incision were re-opposed, and the skin closed using one to two skin staples. Retro-orbital blood samples were collected at ten day intervals. By day twenty post-suture placement, the mouse receiving the highest dose demonstrated a significantly higher hematocrit level than mice receiving the lower dose, all of whom had levels comparable to a non-injected control mouse. These results are summarized in FIG. 2. This elevation in hematocrit level continued for 105 days post-injection, at which time the highest-dose mouse was maintaining a hematocrit in the 65–74% range, with each of the other mice in the 44–50% range (i.e., not significantly different from baseline or from non-injected control) (data not shown). The mice were sacrificed, and bone marrow from the polycythymic mouse prepared and analyzed by a hematopathologist, who confirmed supraphysiologic erythropoiesis in the bone marrow, consistent with increased erythropoietin expression.

EXAMPLE 6

Figure 3:
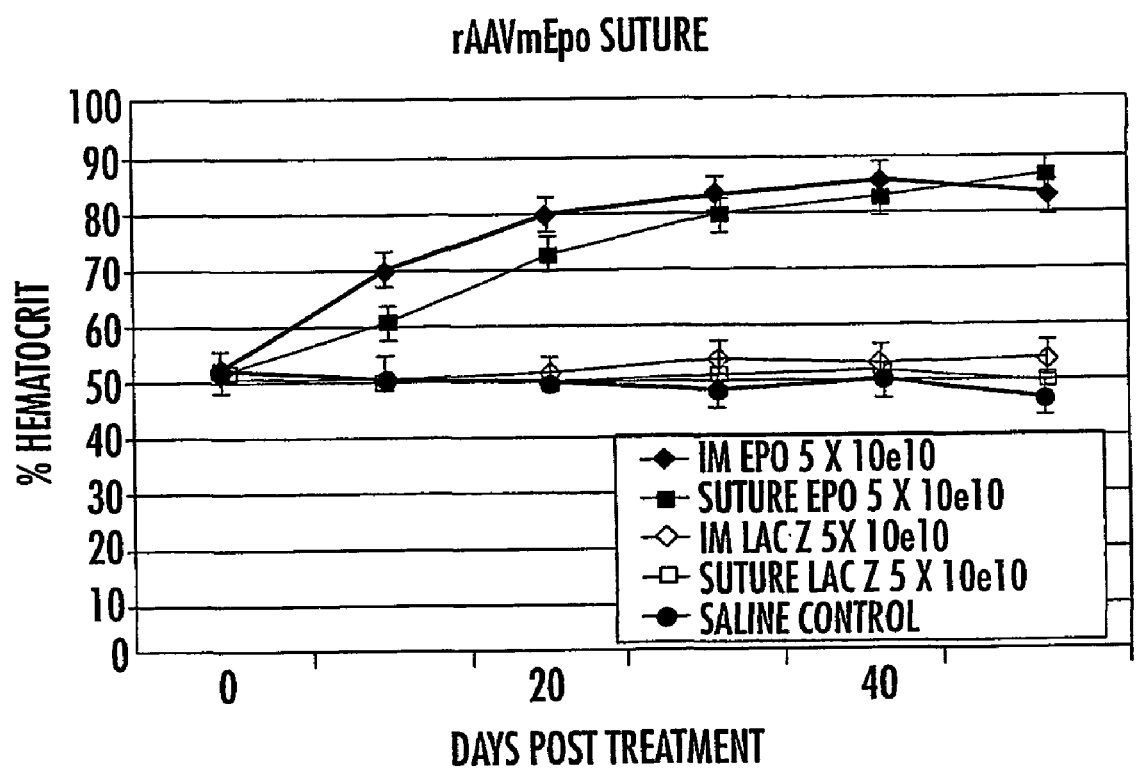
FIG. 3 is a graphical illustration comparing the transduction of rAAV/mEPO delivered intramuscularly and via rAAV/mEPO/suture delivery.

Two additional experiments were conducted in order to support the results set forth above. In one experiment, rAAV/mEpo virus in a standard preparation (dialyzed solution, stored in standard conditions at −20° C., and not desiccated prior to use) was injected intramuscularly in a wide range of doses into BalbC mice, and there appeared to be a threshold dose for increase in hematocrit. Mice receiving 5×10¹⁰ vg showed a marked increase in hematocrit to 80% or above. Therefore, the response of the supersuture mouse with the highest dose is consistent with these intramuscular conditions and results. These results are graphically illustrated in FIG. 3.

Additionally, mice receiving intramuscular suture placement using the braided monofilament sutures impregnated with dessicated rAAV/lacZ actually appeared to show a more marked non-specific scarring response around the suture placement, which appeared to negatively affect expression.

EXAMPLE 7

Gortex® (PTFE) graft material was used as a platform for delivery of dried AAV. GFP gene and human factor IX genes were successfully delivered to cells in tissue culture with the AAV/Gortex®.

HeLa cells were plated at 1×10⁵ cells/well of 6-well plates. All media used on cells was prepared with calf serum which had been prepared with barium sulfate to remove any Vitamin K-dependent clotting factors, including bovine factor IX. Squares of polytetrafluoroethylene (PTFE)-coated vascular graft material (Gore-Tex®, GORE, Flagstaff, Arizona) cut to 0.5×0.5 cm or to 1.0×1.0 cm and autoclaved.

Figure 4:
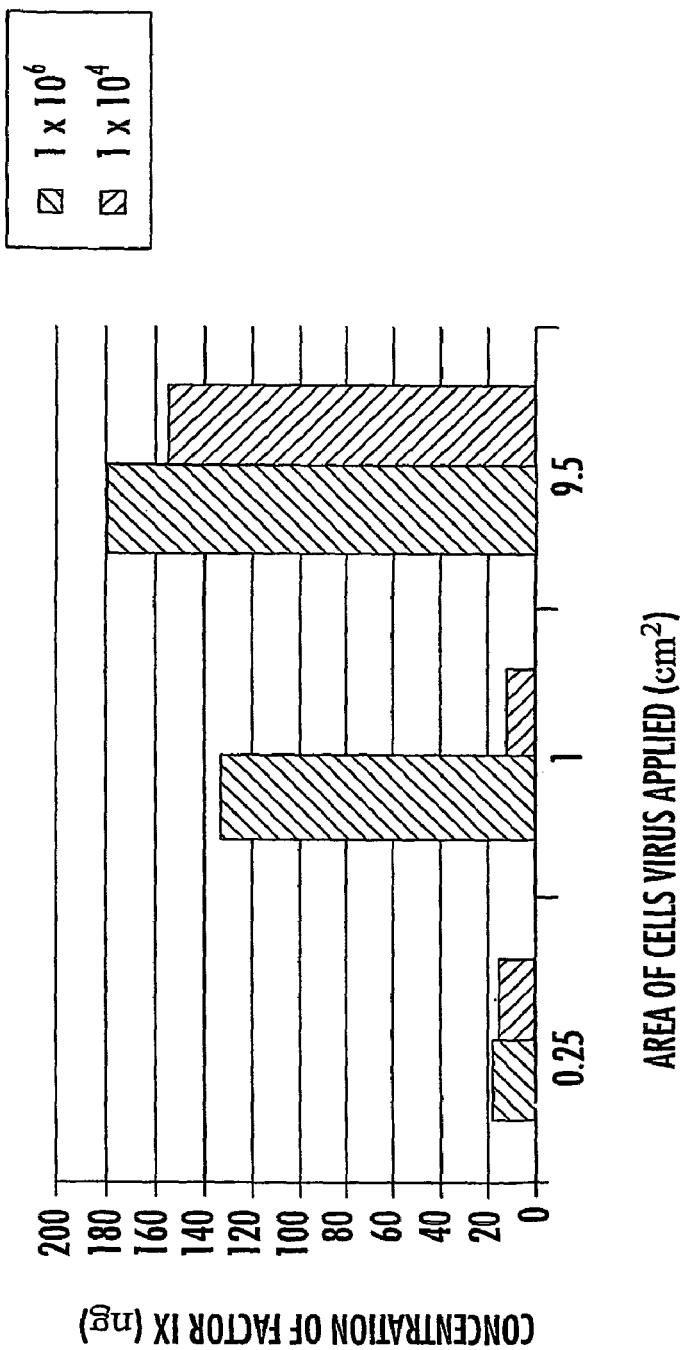
FIG. 4 is a graphical illustration of the successful delivery of GFP gene and human factor IX genes with AAV/Goretex® in tissue culture to cells.

AAV2 prepared with a triple transfection protocol and purified with iodixinol centrifugation and column chromatography was used, with a CAAV promoter driving expression of the gene for human factor IX. Virus at doses to deliver 1×10⁴ virus vector genomes (vg)/cell or 1×10⁶ vg/cell was applied to PTFE matrix. PTFE/AAV overlain onto cells for 1 hour, removed, and cells incubated overnight. On the day following infection, media was replaced with 1.5 ml of factor IX-depleted media. Twenty-four hours later, media was removed, aliquoted and factor IX secreted into the media was quantitated using a sandwich ELISA with antibodies specific for human factor IX, as previously described (Monahan, et al., *Gene Therapy* 5, 40–49 (1998)). The comparison of the two AAV/matrix surface areas (0.25 cm² versus 1.0 cm²) versus virus applied to the entire well (surface area 9.5 cm²) is expressed in FIG. 4 as nanograms of human factor IX expressed per 24 hours.

These experiments suggested that the time for the virus to offload from the surface of the Gortex® (teflon) is very rapid, and further suggest that different delivery platforms may be chosen for different applications to achieve different timecourses and distributions of gene transfer.

EXAMPLE 8

A preparation of rAAV2/murine erythropoietin cDNA virus that was obtained using a method different from the foregoing was used: an identical triple-transfection protocol was used for virus production, however purification of the rAAV was performed to isolate only the rAAV virions that packaged a near-genome length strand of rAAV (so-called "self-complementary rAAV"). Pooled fractions of rAAV containing predominantly self-complementing rAAV/mEpo virions were used to prepare 5.0 absorbable gut suture or aliquoted as virus in solution to yield the same total number of virus particles (=5×10¹⁰ vg) for infections. rAAV/mEpo suture.

Suture material was implanted or virus solution injected intramuscularly into the right quadriceps muscle of Balb/cByJ mice under direct visualization through a 4–5 mm skin incision. Control mice were injected with rAAV/LacZ virus (produced as noted above) in solution or after preparation on suture in a manner identical to the mEpo virus. Sutures were prepared at least 48 hours prior to stitching into place. Whole blood was collected from the retro-orbital venous plexus at day 0 and every 10 days thereafter. Hematocrit was determined by centrifugation of blood in microcapillary tubes. These results indicate that AAV vectors delivered on implantable materials can lead to long-term functional gene expression.

EXAMPLE 9

Figure 5:
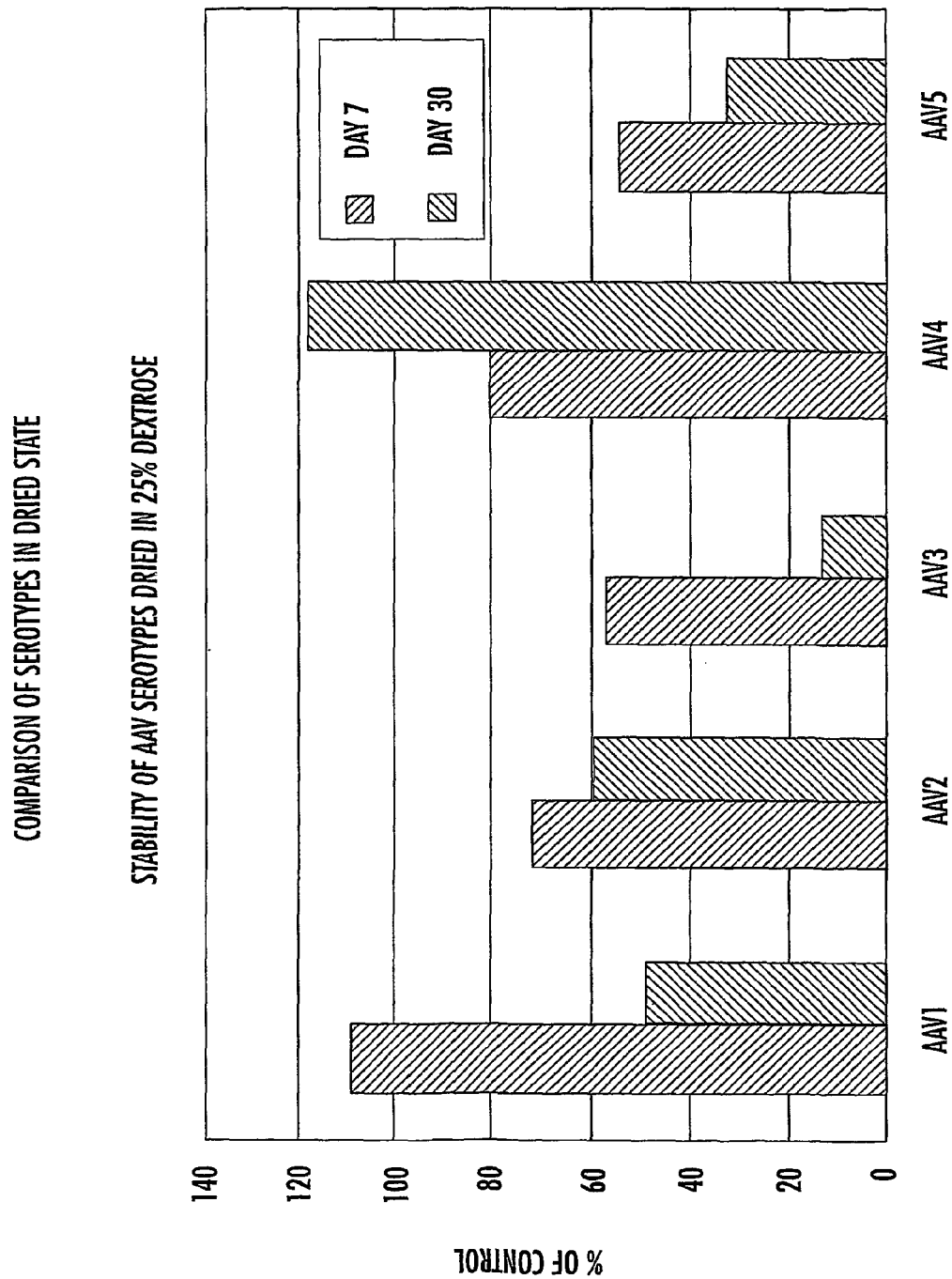
FIG. 5 is a graphical illustration of a sample plot comparing performance of rAAV serotypes 1, 2, 3, 4, and 5 following storage in the dried state in a buffer composed primarily of 25% dextrose solution.

AAV serotype 1, 2, 3, 4, and 5 virus vectors comprising GFP were desiccated in a variety of potential stabilizing buffers including sugars, salt, and/or proteins. Following seven days in the dried state, viruses were resuspended and used to infect cells in monolayer tissue culture. Transduction efficiency was compared to virus that had been maintained in solution on ice without freeze/thaws (i.e., compared as percentage of control). A sample plot of the comparative performance of rAAV serotypes 1, 2, 3, 4, and 5 following storage in the dried state in a buffer composed primarily of 25% dextrose solution is illustrated in FIG. 5.

The foregoing is illustrative of the present invention and is not to be construed as limiting thereof.

The invention claimed is:

1. A method of delivering an adeno-associated virus (AAV) vector to a subject, the method comprising implanting into the subject a surgically implantable matrix comprising an AAV vector dried thereto.

2. The method according to claim 1, wherein the vector is a recombinant AAV (rAAV) vector comprising a heterologous nucleic acid.

3. The method according to claim 2, wherein the heterologous nucleic acid comprises nucleic acid encoding erythropoietin or a bone morphogenic protein.

4. The method according to claim 1, wherein the vector comprises an AAV Type 1 capsid.

5. The method according to claim 1, wherein the vector comprises an AAV Type 2 capsid.

6. The method according to claim 1, wherein the vector comprises an AAV Type 3 capsid.

7. The method according to claim 1, wherein the vector comprises an AAV Type 4 capsid.

8. The method according to claim 1, wherein the vector comprises an AAV Type 5 capsid.

9. The method according to claim 1, wherein the vector comprises an AAV Type 6 capsid.

10. The method according to claim 1, wherein the vector is an AAV Type 1, Type 2, Type 3, Type 4, Type 5 or Type 6 vector.

11. The method according to claim 1, wherein the subject is a human subject.

12. The method according to claim 1, wherein the surgically implantable matrix comprises an implantable device, a surgical graft material, a positively-charged nylon membrane, a suture, cat gut, a tissue scaffold, or a bone graft substitute.

13. The method according to claim 1, wherein the surgically implantable matrix comprises polytetrafluoroethylene (GORTEX™), poliglecaprone (MONOCRYL™), high density polyethylene (MARLEX™), polypropylene, polyglactin, polyd iaxanone (PDS), or polyethylene terephthalate (DACRON™).

14. The method according to claim 1, wherein the AAV vector is a hybrid AAV vector.

15. The method according to claim 1, wherein the AAV vector is a chimeric AAV vector.

16. The method according to claim 1, wherein the AAV vector is a targeted AAV vector.

17. The method according to claim 1, further comprising the step of drying the vector to the surgically implantable matrix.

18. The method according to claim 17, wherein a solution comprising the vector and a stabilizer is dried to the surgically implantable matrix.

19. The method according to claim 18, wherein the stabilizer comprises sugar or sugar alcohol.

20. The method according to claim 17, further comprising storing the surgically implantable matrix comprising the vector dried thereto at room temperature prior to implanting into the subject.

21. The method according to claim 1, wherein the surgically implantable matrix is coated.

22. A surgically implantable matrix comprising a parvovirus vector dried thereto.

23. The surgically implantable matrix according to claim 22, wherein the vector is an adeno-associated virus (AAV) vector.

24. The surgically implantable matrix according to claim 23, wherein the vector comprises an AAV Type 1 capsid.

25. The surgically implantable matrix according to claim 23, wherein the vector comprises an AAV Type 2 capsid.

26. The surgically implantable matrix according to claim 23, wherein the vector comprises an AAV Type 3 capsid.

27. The surgically implantable matrix according to claim 23, wherein the vector comprises an AAV Type 4 capsid.

28. The surgically implantable matrix according to claim 23, wherein the vector comprises an AAV Type 5 capsid.

29. The surgically implantable matrix according to claim 23, wherein the vector comprises an AAV Type 6 capsid.

30. The method according to claim 23, wherein the vector is an AAV Type 1, Type 2, Type 3, Type 4, Type 5 or Type 6 vector.

31. The surgically implantable matrix according to claim 22, wherein the vector is a hybrid parvovirus vector.

32. The surgically implantable matrix according to claim 22, wherein the vector is a chimeric parvovirus vector.

33. The surgically implantable matrix according to claim 22, wherein the vector is a targeted parvovirus vector.

34. The surgically implantable matrix according to claim 22, wherein the vector is a recombinant parvovirus vector comprising a heterologous nucleic acid.

35. The surgically implantable matrix according to claim 34, wherein the heterologous nucleic acid encodes a polypeptide.

36. The surgically implantable matrix according to claim 35, wherein the heterologous nucleic acid encodes factor IX, erythropoietin, superoxide dismutase, globin, leptin, thymidine kinase, catalase, tyrosine hydroxylase, a cytokine, a peptide growth factor or hormone, dystrophin, mini-dystrophin, endostatin, angiostatin, a bone morphogenic protein (BMP), or ornithine transcarbamylase.

37. The surgically implantable matrix according to claim 35, wherein the heterologous nucleic acid encodes a cancer antigen or tumor antigen.

38. The surgically implantable matrix according to claim 35, wherein the heterologous nucleic acid encodes a bacterial antigen, viral antigen, protozoan antigen, or parasite antigen.

39. The surgically implantable matrix according to claim 34, wherein the heterologous nucleic acid encodes an antisense nucleic acid, a ribozyme, an RNA that effects spliceosome-mediated trans-splicing, an interfering RNA (RNAi), a guide RNA, or other non-translated RNA.

40. The surgically implantable matrix according to claim 22, wherein the surgically implantable matrix is stored at room temperature.

41. The surnically implantable matrix according to claim 22, wherein the surgically implantable matrix comprises an implantable device, a surgical graft material, a positively-charged nylon membrane, a suture, cat gut, a tissue scaffold, or a bone graft substitute.

42. The surgically implantable matrix according to claim 22, wherein the surgically implantable matrix comprises polytetrafluoroethylene (GORTEX™), poliglecaprone (MONOCRYL™), high density polyethylene (MARLEX™), polypropylene, polyglactin, polydiaxanone (PDS), or polyethylene terephthalate (DACRON™).

43. The surgically implantable matrix according to claim 22, wherein the surgically implantable matrix is coated.

44. A method of delivering an adeno-associated virus (AAV) vector to a subject, the method comprising implanting into the subject a surgically implantable matrix comprising an AAV vector dried directly thereto.

45. A surgically implantable matrix comprising a parvovirus vector dried directly thereto.

46. A method of delivering an adeno-associated virus (AAV) vector to a subject, the method comprising implanting into the subject a surgically implantable matrix comprising an AAV vector dried thereto, wherein the surgically implantable matrix is produced by the process of drying a liquid comprising the AAV vector to the surgically implantable matrix.

47. A surgically implantable matrix comprising a parvovirus vector dried directly thereto, wherein the surgically implantable matrix is produced by the process of drying a liquid comprising the parvovirus vector to the surgically implantable matrix.

* * * * *

UNITED STATES PATENT AND TRADEMARK OFFICE
CERTIFICATE OF CORRECTION

PATENT NO. : 7,201,898 B2  Page 1 of 1
APPLICATION NO. : 10/276501
DATED : April 10, 2007
INVENTOR(S) : Monahan et al.

It is certified that error appears in the above-identified patent and that said Letters Patent is hereby corrected as shown below:

In The Claims:

Column 21, Claim 13, Line 41:   Please correct "polyd iaxanone"
                                To read -- polydiaxanone--

Column 22, Claim 41, Line 51:   Please correct "surnically"
                                To read --surgically--

Signed and Sealed this

Fourteenth Day of August, 2007

JON W. DUDAS
*Director of the United States Patent and Trademark Office*